US011302013B2

(12) United States Patent
Fenrich et al.

(10) Patent No.: US 11,302,013 B2
(45) Date of Patent: Apr. 12, 2022

(54) SYSTEM AND METHOD FOR IDENTIFYING FEATURES OF A FRICTION RIDGE SIGNATURE BASED ON INFORMATION REPRESENTING A TOPOGRAPHY OF FRICTION RIDGES

(71) Applicant: Identification International, Inc., Blacksburg, VA (US)

(72) Inventors: Richard K. Fenrich, Blacksburg, VA (US); Bryan D. Dickerson, Christiansburg, VA (US)

(73) Assignee: Identification International, Inc., Blacksburg, VA (US)

( * ) Notice: Subject to any disclaimer, the term of this patent is extended or adjusted under 35 U.S.C. 154(b) by 18 days.

(21) Appl. No.: 16/989,394

(22) Filed: Aug. 10, 2020

(65) Prior Publication Data
US 2020/0372656 A1   Nov. 26, 2020

Related U.S. Application Data

(63) Continuation of application No. 15/724,054, filed on Oct. 3, 2017, now Pat. No. 10,740,902.
(Continued)

(51) Int. Cl.
*G06F 21/32* (2013.01)
*A61B 5/107* (2006.01)
(Continued)

(52) U.S. Cl.
CPC .............. *G06T 7/13* (2017.01); *A61B 5/0077* (2013.01); *A61B 5/1079* (2013.01);
(Continued)

(58) Field of Classification Search
CPC ............. G06K 9/0008; G06K 9/00006; G06K 9/00067; A61B 5/1172; A61B 5/0077;
(Continued)

(56) References Cited

U.S. PATENT DOCUMENTS 3,982,836 A   9/1976   Green
4,577,345 A   3/1986   Abramov
(Continued)

FOREIGN PATENT DOCUMENTS

CN   102576265 A   7/2012
CN   103168283 A   6/2013
(Continued)

OTHER PUBLICATIONS

Pang et al. "Extracting Valley-Ridge Lines from Point-Cloud-Based 3D Fingerprint Models." IEEE Computer Graphics and Applications, vol. 33, issue 4, Jul. 2013, pp. 73-81 (Year: 2013).*
(Continued)

*Primary Examiner* — Jon Chang
(74) *Attorney, Agent, or Firm* — Sheppard Mullin Richter & Hampton LLP

(57) ABSTRACT

One or more features of a friction ridge signature of a subject may be identified based on information representing a three-dimensional topography of friction ridges of the subject. Information representing the three-dimensional topography of the friction ridges of the subject may be received. One or more level-three features of the friction ridge signature of the subject may be identified based on the information representing the three-dimensional topography of the friction ridges of the subject. The one or more level-three features may include one or more topographical ridge peaks, topographical ridge notches, topographical ridge passes, pores, and/or other information.

18 Claims, 8 Drawing Sheets

Related U.S. Application Data

(60) Provisional application No. 62/408,684, filed on Oct. 14, 2016.

(51) Int. Cl.

| | | |
|---|---|---|
| *G06V 40/12* | (2022.01) | |
| *G06T 7/00* | (2017.01) | |
| *G06T 7/13* | (2017.01) | |
| *A61B 5/1172* | (2016.01) | |
| *A61B 5/00* | (2006.01) | |
| *B42D 25/313* | (2014.01) | |
| *G06T 7/64* | (2017.01) | |
| *G06T 1/00* | (2006.01) | |
| *A61B 5/01* | (2006.01) | |

(52) U.S. Cl.
CPC .......... *A61B 5/1172* (2013.01); *A61B 5/7239* (2013.01); *B42D 25/313* (2014.10); *G06F 21/32* (2013.01); *G06T 1/0007* (2013.01); *G06T 7/0012* (2013.01); *G06T 7/64* (2017.01); *G06V 40/1347* (2022.01); *G06V 40/1359* (2022.01); *A61B 5/01* (2013.01); *A61B 2562/028* (2013.01); *A61B 2562/0247* (2013.01); *G06T 2200/04* (2013.01); *G06T 2207/30088* (2013.01)

(58) Field of Classification Search
CPC ................ A61B 5/1079; A61B 5/7239; A61B 2562/0247; A61B 5/01; A61B 2562/028; G06F 21/32; G06V 40/1359; G06V 40/1347; G06T 7/13; G06T 7/64; G06T 1/0007; G06T 7/0012; G06T 2200/04; G06T 2207/30088; B42D 25/313
See application file for complete search history.

(56) References Cited

U.S. PATENT DOCUMENTS

| | | | |
|---|---|---|---|
| 5,400,662 A | 3/1995 | Tamori | |
| 7,274,396 B2 | 9/2007 | Bock | |
| 7,766,826 B2 | 8/2010 | Lee | |
| 8,224,064 B1 * | 7/2012 | Hassebrook | G06T 7/521 |
| | | | 382/154 |
| 8,265,352 B1 | 9/2012 | Neoh | |
| 8,736,581 B2 | 5/2014 | Han | |
| 9,848,130 B2 | 12/2017 | Legakis | |
| 2002/0027605 A1 | 3/2002 | Lee | |
| 2003/0149662 A1 | 8/2003 | Shore | |
| 2006/0018519 A1 | 1/2006 | Siegel | |
| 2006/0227263 A1 | 10/2006 | Kunai | |
| 2007/0075138 A1 | 4/2007 | Ross | |
| 2007/0153258 A1 | 7/2007 | Hernandez | |
| 2007/0165914 A1 | 7/2007 | Werthiem | |
| 2008/0056539 A1 | 3/2008 | Sweeney | |
| 2008/0187190 A1 | 8/2008 | Shin | |
| 2009/0034803 A1 | 2/2009 | Matos | |
| 2010/0101961 A1 | 4/2010 | Lee | |
| 2010/0302210 A1 | 12/2010 | Han | |
| 2011/0096025 A1 | 4/2011 | Slobodin | |
| 2011/0186712 A1 | 8/2011 | Blenkhorn | |
| 2011/0216948 A1 | 9/2011 | Yalla | |
| 2013/0202182 A1 | 8/2013 | Rowe | |
| 2013/0272585 A1 | 10/2013 | Mueller | |
| 2014/0337948 A1 | 11/2014 | Hoyos | |
| 2015/0261367 A1 | 9/2015 | Zhang | |
| 2016/0292491 A1 | 10/2016 | Dickerson | |
| 2016/0379039 A1 | 12/2016 | Dagan | |
| 2017/0235994 A1 | 8/2017 | Yang | |
| 2017/0316248 A1 | 11/2017 | He | |
| 2018/0225498 A1 | 8/2018 | Setlak | |

FOREIGN PATENT DOCUMENTS

| | | |
|---|---|---|
| CN | 2016100882913 | 2/2016 |
| EP | 0514182 A1 | 11/1992 |
| EP | 0867828 A2 | 9/1998 |
| GB | 2243235 A | 10/1991 |
| JP | 02149253 A | 6/1990 |
| JP | 2004171307 A | 6/2004 |
| JP | 2007529811 A | 10/2007 |
| KR | 1020090060283 | 6/2009 |
| WO | WO9811499 | 3/1998 |
| WO | 2008017077 | 2/2008 |
| WO | 2010056177 A1 | 5/2010 |
| WO | 2014030129 A1 | 2/2014 |
| WO | 2014057171 A1 | 4/2014 |
| WO | 2017105318 A1 | 6/2017 |

OTHER PUBLICATIONS

European Patent Application No. 17860890.7, Extended European Search Report dated Apr. 24, 2020, 7 pages.
Fan, et al. Fractal Design Concepts for Stretchable Electronics. Nature Communications. Feb. 7, 28, 29, 2014. (Retrieved Jul. 6, 2016). Retrieved from internet<URL:http://www.nature.com/ncomms/2014/140207/ncomms4266/pdf/ncomms4266.pdf> pp. 1-8.
International Search Report and Written Opinion for PCTIB1756374, dated Jan. 18, 2018, 11 pages.
International Search Report and Written Opinion for PCTIB1756375, dated Feb. 9, 2018. 18 pages.
Korean Patent Application No. 10-2019-7013803, Notice of Preliminary Rejection dated May 21, 2020, with English translation, 15 pages.
Machine Translation for CN 201610088291.3, filed Feb. 17, 2016, 21 pages.
S.C.B. Mannsfeld et al. Highly Sensitive Flexible Pressure Sensors with Micro-structured 7, 15, 23, 27 Rubber Dielectric Layers. Nature Materials 9, 859-864 (2010). [Retrieved Jul. 6, 2016) Retrieved from internet<http://www-ssrl.slac.stanford.edu/research/highlights_archive/pressuresensor> p. 859-864.
Short, Nathaniel J., et al., "Temporal Analysis of Fingerprint Impressions", 2012 IEEE Fifth International Conference an Biometrics: Theory, Applications and Systems (BTAS), Sep. 23, 2012 (Sep. 23, 2012), XP032276547, DOI: 10.1109/BTAS.2012.6374601 ISBN: 978-1-4673-1384-1, pp. 359-364.

* cited by examiner

710

720

730

SYSTEM AND METHOD FOR IDENTIFYING FEATURES OF A FRICTION RIDGE SIGNATURE BASED ON INFORMATION REPRESENTING A TOPOGRAPHY OF FRICTION RIDGES

CROSS-REFERENCE TO RELATED APPLICATION

This application is a continuation of U.S. patent application Ser. No. 15/724,054, filed Oct. 3, 2017, entitled "SYSTEM AND METHOD FOR IDENTIFYING FEATURES OF A FRICTION RIDGE SIGNATURE BASED ON INFORMATION REPRESENTING A TOPOGRAPHY OF FRICTION RIDGES", which claims priority to U.S. Provisional Patent Application Ser. No. 62/408,684, filed Oct. 14, 2016, entitled "SYSTEM AND METHOD FOR IDENTIFYING FEATURES OF A FRICTION RIDGE SIGNATURE BASED ON INFORMATION REPRESENTING A TOPOGRAPHY OF FRICTION RIDGES", which are hereby incorporated herein by reference in their entirety.

FIELD OF THE DISCLOSURE

This disclosure relates to a system and a method for identifying features of a friction ridge signature of a subject based on information representing a topography of friction ridges of the subject.

BACKGROUND

Fingerprints (i.e., friction ridge signatures) illustrate a pattern of friction ridges and valleys having features that may be identified. In two-dimensional fingerprint representations associated with existing fingerprint imaging technology, the top of the friction ridges appear to be flat and/or planar. However, friction ridges that make up the friction ridge pattern reflected in a fingerprint are more like mountain ranges, undulating up and down with areas of lower elevation and areas where peaks exist. These variations are not visible in typical fingerprints because the subject's finger is pressed against an imaging surface causing the peaks and undulating areas to flatten such that they are captured as if they were flat. As such, these variations are ignored and are not visible as identification features.

Instead, conventional fingerprint classification and identification methods focus on the type and location of level I and level II features. Level I features, such as loops, arches, tents, deltas, and whorls, are mainly used to classify or subdivide fingerprints into broad categories, but do not provide sufficient discriminating power to identify individuals.

Level II features, such as ridge endings, bifurcations, and dots provide the basis of present day fingerprint identification algorithms. These features are classifications of the continuity of fingerprint ridge lines. To automate this process, the contrast of fingerprint images is often increased so that image processing algorithms can more accurately follow ridge lines to locate deviations from ridge line continuity. Relational maps of level II features are compared to national databases in order to identify individuals by their fingerprints.

Additional Level III features broadly arise from fine details of fingerprint patterns, ridges and valleys. Typical level III details may include ridge shape, width, and path deviation, pores, incipient ridges, breaks, creases, scars, and/or a variety of ridge edge contour details. Human experts may use Level III features to confirm the identity of an individual after a preliminary match based on level II features. Unfortunately, some level III features show significant variability within the same individual from fingerprints taken under different conditions. These factors have so far raised significant challenges for the use of level III features in automated fingerprint recognition algorithms.

SUMMARY

One aspect of the disclosure relates to identifying features of a friction ridge signature of a subject based on information representing a topography of friction ridges of the subject. The friction ridges of the subject may vary in elevation, having one or more ridge peaks, ridge notches, ridge pores, and/or other three-dimensional structures and/or features. The friction ridges of the subject form a friction ridge pattern that may therefore have three dimensional features. The three dimensional features may be reflected in the friction ridge signature of the subject according to the systems and methods described herein. For example, a topographical representation of the three-dimensional friction ridge structures and/or of the friction ridge pattern may be used as a new basis for fingerprint identification. The three-dimensional friction ridge structures may include one or more of topographical ridge peaks, topographical ridge notches, topographical ridge passes, pores, and/or other three-dimensional friction ridge structures. By way of non-limiting example, the topographical ridge peaks may be used as level III fingerprint features that are permanent, abundant, not typically displayed by conventional methods, and form the a basis of for a new robust fingerprint identification strategy.

Three-dimensional features may be identified in the friction ridge signature of the subject based on information representing the three-dimensional topography of the friction ridges of the subject. The information representing the three-dimensional topography of the subject may include three-dimensional information. The level III features identified based on the information representing the three-dimensional topography of the friction ridges of the subjects may include one or more of topographical ridge peaks, topographical ridge notches, topographical ridge passes, pores, and/or other features.

Topographical ridge peaks may include one or more high (e.g., high elevation, etc.) points, local apexes, crests, and/or peaks of a friction ridge. A topographical ridge pass may include a path across a friction ridge that has a lower height and/or elevation than the surrounding friction ridge. A topographical notch may include one or more of an indentation, a dent, an impression, a depression, a cut out, and/or an imprint in the edge (and/or surface) of one or more friction ridges. A pore may include an orifice and/or hole in a friction ridge of a subject.

The system may include one or more processors. The one or more processors may communicate with one or more imaging systems. By way of non-limiting example, the imaging systems may include one or more of total internal reflection based imaging systems (i.e., TIR imaging systems), electroluminescent imaging systems (also known as electro-optical imaging or light emitting sensors), ultrasound scanners, three-dimensional scanners, other scanners, capacitive array imaging systems, pyro-electric (or thermal) imaging systems, radio frequency (RF) imaging systems, pressure sensor imaging systems, micro electro-mechanical devices, other optical sensor imaging systems, pressure sensitive membranes used with optical or electrical imaging systems, a three-dimensional structured light scanner, a three-dimensional camera, a three-dimensional imaging system, and/or other two dimensional or three dimensional imaging system(s) and/or system(s). The imaging surface may be rigid, flexible, curved, and/or have other characteristics.

The one or more processors may be configured by machine-readable instructions. The machine-readable instructions may be configured to execute one or more components. The components including one or more of an information component, an feature identification component, a matching component, and/or other components.

One or more processors may be configured to receive information representing the three-dimensional topography of the friction ridges of the subject. The information representing the three-dimensional topography of the friction ridges of the subject may be received by the information component. In some implementations, the information representing the three-dimensional topography of the friction ridges of the subject may be generated and/or provided by one or more imaging system(s) and/or systems.

The information representing the three-dimensional topography of the friction ridges may include any three dimensional information that describes the surface of one or more friction ridges of the subject. The information representing the three-dimensional topography of the friction ridges of the subject may be in two-dimensional and/or three-dimensional format. By way of non-limiting example, the information representing the three-dimensional topography of the friction ridges may include one or more of: a topographical map, a pressure map, a gradient map (e.g., illustrating slopes and/or gradients of the friction ridges) one or more cross sectional shapes of the friction ridge pattern at different elevations, a series of images captured over a time period by a an imaging system (with and/or without a pressure sensitive membrane), a three-dimensional image, a three-dimensional data point cloud, a three-dimensional model, and/or other information.

Feature identification component may be configured to identify one or more level III features based on the information representing the three-dimensional topography of the friction ridges of the subject, and/or other information. The one or more level III features may include one or more topographical ridge peaks, topographical ridge notches, topographical ridge passes, pores, and/or other features.

Matching component may be configured to compare one or more of the topographical ridge peaks, the topographical ridge notches, the topographical ridge passes, the pores, and/or other features of the friction ridge signature of the subject with one or more topographical ridge peaks, topographical ridge notches, topographical ridge passes, pores, and/or other features of a second friction ridge signature. The matching component may determine whether the friction ridge signature of the subject matches the second friction ridge signature.

Although this description primarily references friction ridges located on a human finger and/or hand, it is considered to be applicable to any place on the human body having friction ridges and/or a friction ridge pattern (e.g., such as a foot, toe, heel, palm, and/or other parts of the body).

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
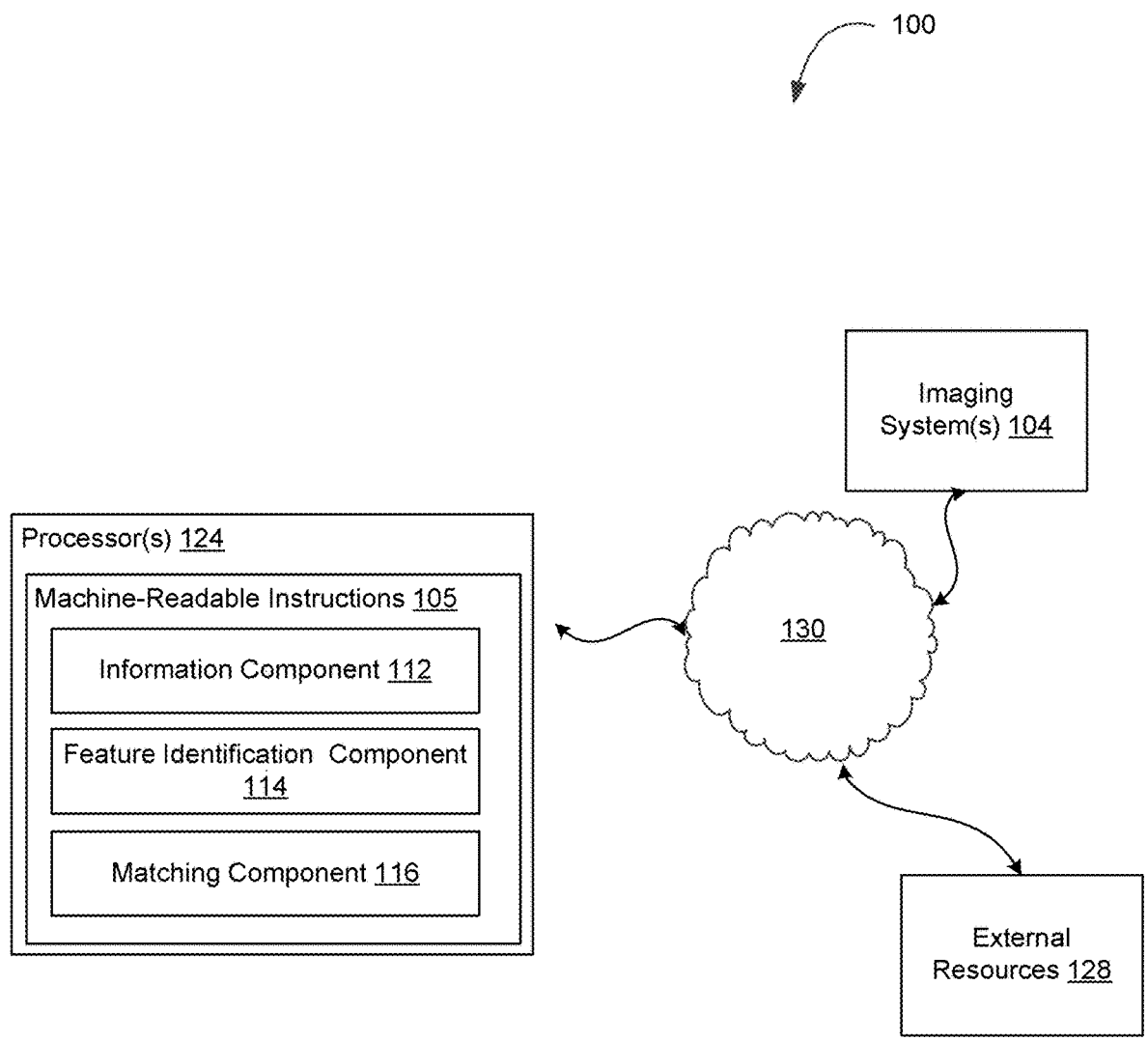
FIG. 1 illustrates a system configured to identify features of a friction ridge signature of a subject, in accordance with one or more implementations.

FIG. 1 illustrates a system 100 configured to identify features of a friction ridge signature of a subject. A friction ridge signature (i.e., fingerprint) may include an impression left by the friction ridges of a human hand (e.g., the pad of a human finger, a human palm, etc.). System 100 described herein may identify features of a friction ridge signature of a subject based on information representing a topography of the friction ridges of the subject. The friction ridges of a subject may form a friction ridge pattern represented in the friction ridge signature. The friction ridges of the subject may vary in height/elevation and/or have three dimensional features. By way of non-limiting example, individual ones of the friction ridges of a subject may have one or more peaks, ridges, notches, pores, and/or other three dimensional features. As such, the friction ridge pattern of a subject may have three dimensional features that are currently not identified by present fingerprinting methods.

Conventional fingerprint classification and identification methods focus on the type and location of level I and level II features of a fingerprint (i.e., friction ridge signature). Level I features, such as loops, arches, tents, deltas, and/or whorls, are typically used to classify or subdivide fingerprints into broad categories. Level I features may not provide sufficient discriminating power to identify individuals.

Level II features, such as ridge endings, bifurcations, and dots provide the basis of present day fingerprint identification algorithms. These features are classifications of the continuity of fingerprint ridge lines. To automate the identification process, the contrast of fingerprint images in existing technology may be increased so that image processing algorithms can more accurately follow ridge lines to locate deviations from ridge line continuity. Relational maps of level II features are compared to databases of reference features in order to identify individuals by their fingerprints. Level two features are two dimensional.

Level-three (i.e., Level III) features arise from fine details of fingerprint patterns, ridges and valleys. Typical level III details may include two dimensional representations of ridge shape, width, path deviation, pores, incipient ridges, breaks, creases, scars, and/or ridge edge contour details. Human experts may use one or more Level III features to confirm the identity of an individual after a preliminary match based on level II features. However, level III features show significant variability within the same individual from fingerprints taken under different conditions. These factors raise significant challenges for the use of level II features in automated fingerprint recognition algorithms based on current systems and methods.

However, as described herein, new level III features may be identified based on information representing the three-dimensional topography of the friction ridges of a subject. These three-dimensional features may be identified in the friction ridge signature of the subject based on the information representing the three-dimensional topography of the friction ridges of the subject. As such, a representation of three-dimensional friction ridge structures may be used as a new basis for fingerprint identification. The level III features identified based on the information representing the three-dimensional topography of the friction ridges of the subjects may include one or more of topographical ridge peaks, topographical ridge notches, topographical ridge passes, pores, and/or other features. The topographical ridge peaks, topographical ridge notches, topographical ridge passes, and/or other features may be three-dimensional structures of the friction ridge pattern.

Topographical ridge peaks may include one or more high (e.g., high elevation, etc.) points, local apexes, crests, and/or peaks of a friction ridge. An individual friction ridge may include one or more topographical ridge peaks. A topographical ridge pass may include a path across a friction ridge that has a lower height and/or elevation. In some implementations, a topographical ridge pass may include a lower elevation pass or path between one or more topographical ridge peaks. The topographical ridge pass may vary in elevation.

A topographical notch may include one or more of an indentation, a dent, an impression, a depression, a cut out, and/or an imprint in the surface and/or edge of one or more friction ridges. By way of non-limiting example, a topographical notch may include an indentation on an edge of the three-dimensional friction ridge. Continuing the non-limiting example, the indentation on the edge of the friction ridge may not extend through the friction ridge uniformly. A pore may include an orifice and/or hole in a friction ridge of a subject. Pores may generally be known as level II features, however pores may only be displayed by imaging systems (e.g., a TIR based imaging system, etc.) when the pores are inactive because the moisture in active pores may cause index matching (e.g., which makes the pore appear black, just like surrounding ridge tissue in contact with the imaging surface). In previous systems, where a single frame that does not represent the topography of the friction ridges is used to identify friction ridge pattern features, pores may be unreliable features. Under various amounts of pressure, a pore may appear to be a notch and/or vice versa. Identifying level III features based on information representing the three-dimensional topography of the friction ridges of the subject may eliminate these issues. For example, a true notch will not close into a pore, even as additional pressure is applied in subsequent images of the same sequence. If a notch feature appears closed like a pore at some pressure, that feature is actually a pore, and not a notch.

For example, at different cross-sectional elevations of the friction ridge pattern, one or more of the topographical ridge peaks, topographical ridge notches, topographical ridge passes, pores, and/or other features may and/or may not be detectable. As a subject presses his finger on a pressure sensitive membrane, one or more of the topographical ridge peaks, topographical ridge notches, topographical ridge passes, pores, and/or other features may change with varied amounts of applied pressure. As pressure is applied, the three dimensional features may flatten and/or augment making them undetectable in existing friction ridge signatures. However, such features may be identifiable in information representing the three-dimensional topography of the friction ridges of the subject.

In some implementations, one or more of the topographical ridge peaks may be identified based on one or more of a region in a topographical map having a higher elevation level than surrounding regions; a region in the pressure map having a higher relative pressure than surrounding regions; an isolated island in the cross sectional shapes of the friction ridge pattern at different elevations; a set of negative surface gradients measured in multiple directions from a topographical ridge peak. In some implementations, the multiple directions from the topographical ridge peak may include four directions comprising the positive and negative directions of two orthogonal axes in a 2-dimensional representation of the three-dimensional topography of the friction ridges of the subject. In some implementations, the multiple directions from the topographical ridge peak may include two or three directions that may be separated by ninety degrees and/or approximately ninety degrees. In some implementations, the multiple directions from the topographical ridge peak may include two or more directions that go away from each other. Other suitable examples of identifying topographical ridge peaks based on negative surface gradients measured in multiple directions are contemplated.

One or more of the topographical ridge passes may be identified based on one or more of: a region in the topographical map having an elevation level that is higher than the nearest valleys and lower than the nearest peaks; a region in the pressure map having a higher relative pressure than the nearest valleys and a lower relative pressure than the nearest pressure peaks; a continuous friction ridge shape at an intermediate and lower elevations but not at higher elevations in cross sections the of the friction ridge pattern at different elevations; a set of negative or near zero slopes or pressure gradients measured in two first opposite directions along with two positive slopes or pressure gradients in two other opposite directions that are orthogonal to the first opposite directions going out from the ridge pass location; and/or based on other characteristics of the information representing the three-dimensional topography of the friction ridges of the subject.

One or more pores may be identified based on one or more of the following criteria: a region in the topographical map having an elevation level that is lower than the surrounding friction ridge elevation in all directions; a region in the pressure map having a lower relative pressure than the surrounding friction ridge pressure in all directions; a hole in the cross section the of the friction ridge pattern at different depths; a set of positive pressure gradients measured in multiple directions going out from a pore location (e.g., the multiple directions may include four directions comprising the positive and negative directions of two orthogonal axes in a 2-dimensional representation of the three-dimensional topography of the friction ridges of the subject, two or three directions that may be separated by ninety degrees and/or approximately ninety degrees, and/or two or more directions that go away from each other). Other suitable examples of identifying topographical ridge peaks based on negative surface gradients measured in multiple directions are contemplated; and/or based on other characteristics of the information representing the three-dimensional topography of the friction ridges of the subject.

One or more of the topographical ridge notches may be identified based on one or more of: a region in the cross sectional shapes of the friction ridge patterns at different elevations having a local positive curvature in the direction towards the nearest valley; a set of positive pressure gradients measured in multiple directions (e.g., three of the four directions comprising the positive and negative directions of two orthogonal axes in a 2-dimensional representation of the three-dimensional topography of the friction ridges of the subject, two or three directions that may be separated by ninety degrees and/or approximately ninety degrees, and/or two or more directions that go away from each other) along with 1 negative slope and/or surface gradient in a remaining direction going out from a topographical ridge notch location; and/or based on other characteristics of the information representing the three-dimensional topography of the friction ridges of the subject. In some implementations, in order to be correctly identified as a topographical ridge notch, the location must not exhibit the conditions by which a pore may be identified (e.g., see above). A correctly identified topographical ridge notice may not exhibit the conditions by which a pore may be identified when analyzing images of the friction ridge acquired at different times, and/or the information representing the three-dimensional topography of the subject.

Figure 2:
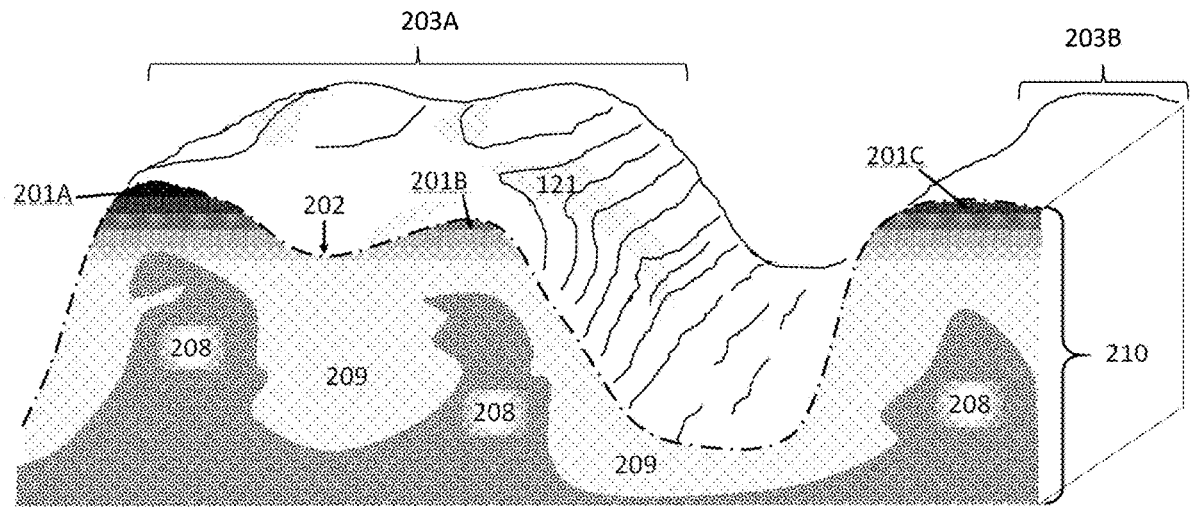
FIG. 2 illustrates a cross section of a portion of a friction ridge pattern of a subject, in accordance with one or more implementations.

FIG. 2 illustrates a cross section of a portion of a friction ridge pattern of a subject, in accordance with one or more implementations. The portion of friction ridge pattern 200 may include topographical ridge peaks 201A, 201B, 201C; a topographical ridge notch 121; a topographical ridge pass 202; and/or other features. Topographical ridge peaks 201 may include one or more high points or sections of the topography of the friction ridges. Topographical ridge pass 202 may include a lower elevation portion of friction ridge 203A. In some implementations, topographical ridge pass 202 may be located between topographical ridge peaks 201. Topographical notch 121 may include an indentation in the edge and/or surface of friction ridge 203A. Topographical notch 121 may be an indentation that begins in the surface of friction ridge 203A near the edge, and gradually merges into the edge of friction ridge 203A and/or valley 209.

In some implementations, friction ridge tissue 210 may include dermal papillae 208. Dermal papillae 208 may comprise tiny lumps in the dermis that extend into the epidermis 209. In friction ridge patterns of a subject, friction ridges may contain one or more (e.g., two, etc.) rows of dermal papillae 208, one just inside each edge of the ridge. The location of dermal papillae 208 may correspond with peaks in the epidermis ridge structure and/or topographical ridge peaks 201.

Returning to FIG. 1, in some implementations system 100 may include one or more processor(s) 124. The one or more processor(s) 124 may be configured to communicate with one or more imaging system(s) 104. One or more processor(s) 124 may be configured to execute machine-readable instructions 105 to implement system components. The system components may include one or more of an information component 112, a feature identification component 114, a matching component 116, and/or other components.

Imaging system(s) 104 may include one or more of a total internal reflection based imaging system (i.e., TIR-based imaging system)), electroluminescent imaging systems (also known as electro-optical imaging or light emitting sensors), ultrasound scanners, three-dimensional scanners, other scanners, capacitive array imaging systems, pyro-electric (or thermal) imaging systems, radio frequency (RF) imaging systems, pressure sensor imaging systems, micro electro-mechanical devices, other optical sensor imaging systems, pressure sensitive membranes used with optical or electrical imaging systems, a three-dimensional structured light scanner, a three-dimensional camera, a three-dimensional imaging system, and/or other two-dimensional or three-dimensional imaging system(s). Total internal reflection is a known concept based on light traveling at different speeds in different materials. A refractive index, ni, of a material, i, is the speed of light in a vacuum, c, divided by the velocity of light in the material, vi: ni=c/vi. As light passes from one material to another, the change of speed results in refraction. Measured from perpendicular to the surface, the angle of incidence, 81, and the angle of refraction, 82, are given by Snell's law: n1 sin(81)=n2 sin(82). Accordingly, when light emerges from a glass block (n1–1.5) into air (n2=1), the light will be refracted away from the perpendicular to the surface. That is, 82>81 because n1>n2. At a critical angle of incidence, 8c, 82 becomes 90° as the refracted light runs along the glass-air surface to form an evanescent wave. When 81>8c, the incident light is reflected back into the glass by a process called total internal reflection (TIR). Changes in TIR may serve to generate an image of an applied fingerprint. The intensity of light reflected from the imaging surface at a particular location may be altered according to several optical mechanisms. For example, changing the local effective refractive index n2 on or near the glass-air surface (by touching a finger or other material to the glass prism) may absorb or scatter the refracted ray or the evanescent wave.

TIR-based imaging systems are generally known in the art. Such systems have been developed to capture images of fingerprints using a prism (e.g., glass or plastic). The prism may be a platen. In TIR-based imaging systems, a light beam from a light source is typically directed at a face of the prism at the critical angle. Incident angles beyond the critical angle will cause the propagating light to totally internal reflect in the prism and pass out through the opposing side. When a finger is placed on the prism face where TIR occurs, it changes the boundary conditions such that where friction ridges make contact with the prism surface, the light wave is disrupted and largely attenuated by the skin. Where the friction ridges do not make contact, the light is totally internally reflected by the interface and captured by a camera or sensor oriented to view the surface from the reflection angle matching the source angle of incidence. Light scattered or absorbed by the finger reduces the local light intensity in an image captured by the camera or the sensor. The result is high contrast fingerprint images from the prism surface scene such that the background appears light and a fingerprint (i.e., friction ridge signature) appears dark since the TIR is reduced by the friction ridges. In some implementations, imaging system(s) 104 may include a live scan imaging system.

As a subject presses their finger in contact with an imaging surface (e.g., the contact side of a prism in a TIR-based imaging system as a non-limiting example), the surface area of the imaging surface engaged by the friction ridges of the subject increases over time. The highest portions of the friction ridges come into contact with the imaging surface before the lower portions of the friction ridges. As more pressure is applied by the subject, the friction ridges may flatten. The compression and/or flattening of the friction ridges may effectuate an increase the surface area of the imaging surface that is engaged with the friction ridges of the subject. In typical two-dimensional fingerprints known in the art, the friction ridge signature represents flattened friction ridges such that they appear to be flat and/or planar ridges surrounded by valleys or gaps between the ridges.

In some implementations, the information representing the three-dimensional topography of the friction ridges may be generated one or more imaging systems and/or captured as a sequence of images. The individual images in the sequence of images may indicate which portions of the imaging surface are engaged by the friction ridges of the subject at the time the image was captured. Over a time period in which the sequence of images are captured, the surface area of the imaging surface engaged by the friction ridge pattern of the subject may increase due to increasing compression of the friction ridge pattern on the imaging surface. The images in the sequence may be aggregated such that the aggregation representation depicts cross sectional shapes of the friction ridge pattern at different elevations which may be determined from the individual images of the surface area of the imaging surface engaged by the friction ridge pattern. As such, the aggregation representation may indicate the relative changes in elevation and/or shape of the topography of the friction ridges. In some implementations, the information representing the three-dimensional topography of the friction ridges may include the aggregation representation.

In some implementations, a TIR-based system may have a pressure sensitive membrane. The pressure sensitive membrane may be coupled to the imaging surface of the TIR-based imaging system such that the subject presses their finger on the pressure sensitive membrane. By way of non-limiting example, the pressure sensitive membrane may be the same as or similar to the pressure sensitive membrane embodiments, and/or the systems and methods described in U.S. patent application Ser. No. 15/091,532, entitled "SYSTEMS AND METHODS FOR CAPTURING IMAGES USING A PRESSURE SENSITIVE MEMBRANE," filed Apr. 5, 2016, the foregoing being incorporated herein by reference in its entirety.

Figure 3:
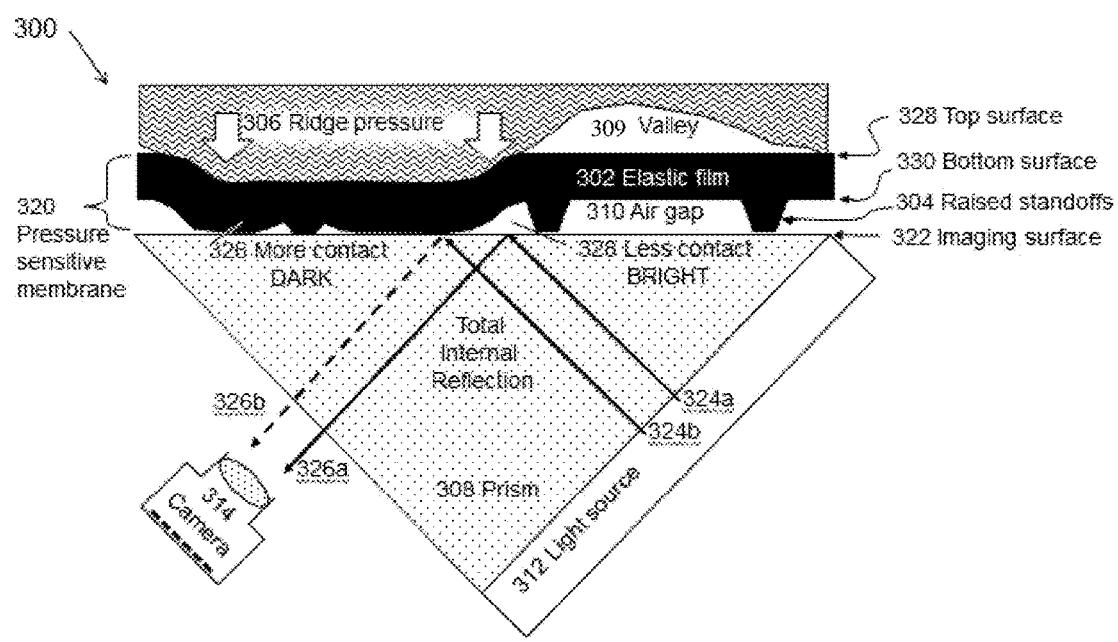
FIG. 3 illustrates a TIR-based imaging system with a pressure sensitive membrane, in accordance with one or more implementations.

By way of non-limiting example, FIG. 3 illustrates a TIR-based imaging system 300 with a pressure sensitive membrane 320. The texture on the bottom surface 330 of the elastic film 302 may contain raised standoffs 304. Raised standoffs 304 may create a thin air gap 310 between elastic film 302 and imaging surface 322 of prism 308. Under a valley 309, air gap 310 may be maintained. Therefore, there may be less contact between elastic film 302 and imaging surface 322. When light ray 324a travels from light source 312 to imaging surface 322, it may undergo total internal reflection and may be detected by the camera 314 (and/or a sensor) as a local bright spot 328, so that valley 304 appears bright in a TIR image. A separate light ray 324b may reach the imaging surface 322 directly under applied ridge pressure 306. Under applied ridge pressure 306, the elastic film 302 may be deflected towards imaging surface 322 and/or may make more contact 326 with imaging surface 322. This contact 326 with the index matched and light absorbing material in the elastic film 302 may cause some of light ray 324b to refract into the film and be absorbed. Reflected light ray 326b may have a lower intensity when it reaches camera 314 (and/or a sensor). As such, camera 314 (and/or a sensor) may image regions under ridge 306 through pressure sensitive membrane 320 as darker.

Returning to FIG. 1, processors 124 may be configured to receive information representing the three-dimensional topography of the friction ridges of the subject. The information representing the three-dimensional topography of the friction ridges of the subject may be received at information component 112. The information representing the three-dimensional topography of the friction ridges of the subject may be received from one or more imaging system(s) 104 (e.g., one or more of a TIR-based imaging system, a TIR-based imaging system having a pressure sensitive membrane, electroluminescent imaging systems (also known as electro-optical imaging or light emitting sensors), ultrasound scanners, three-dimensional scanners, other scanners, capacitive array imaging systems, pyro-electric (or thermal) imaging systems, radio frequency (RF) imaging systems, pressure sensor imaging systems, micro electro-mechanical devices, other optical sensor imaging systems, pressure sensitive membranes used with optical or electrical imaging systems, a three-dimensional structured light scanner, a three-dimensional camera, a three-dimensional imaging system, and/or other two-dimensional or three-dimensional imaging system(s)).

The information representing the three-dimensional topography of the friction ridges may include any information that indicates depth and/or elevation variations of one or more three-dimensional features of the friction-ridge pattern of a subject. The information representing the three-dimensional topography of the friction ridges may include three dimensional information (e.g., in two-dimensional and/or three-dimensional format) that describes the surface of one or more friction ridges of the subject. In some implementations, the information representing the three-dimensional topography of the friction ridges of the subject may include information representing three-dimensional structures and/or features of the friction ridges formatted as two dimensional information (e.g., a topographical map, pressure map, etc.). In some implementations, the information representing the three-dimensional topography of the friction ridges may include three-dimensional information in a three-dimensional format (e.g., a three-dimensional image, a three-dimensional point cloud, rendering, model, etc.).

By way of non-limiting example, the information representing the three-dimensional topography of the friction ridges may include one or more of: a topographical map, a pressure map, a gradient map, one or more cross sectional shapes of the friction ridge pattern at different elevations, a series of images captured over a time period by a total internal reflection based imaging system (with and/or without a pressure sensitive membrane), a three-dimensional image, a three-dimensional model, and/or other information. In some implementations, the cross sectional shapes may not represent entirely straight and/or uniform cuts due to the subject applying various amounts of pressure, the imaging surface being flexible and/or curved, and/or for other reasons. By way of non-limiting example, the cross sectional shapes may include contours generated based on changes in areas of engagement between a friction ridge pattern and an imaging surface as a series of images are captured over time. One or more gradients and/or slopes may be determined based on the contours. These examples are not intended to be limiting and other information representing three dimensional features of the friction ridges of a subject may be used to identify one or more topographical ridge peaks, topographical ridge notches, topographical ridge passes, pores, and/or other level III features of a friction ridge pattern of a subject.

Figure 4:
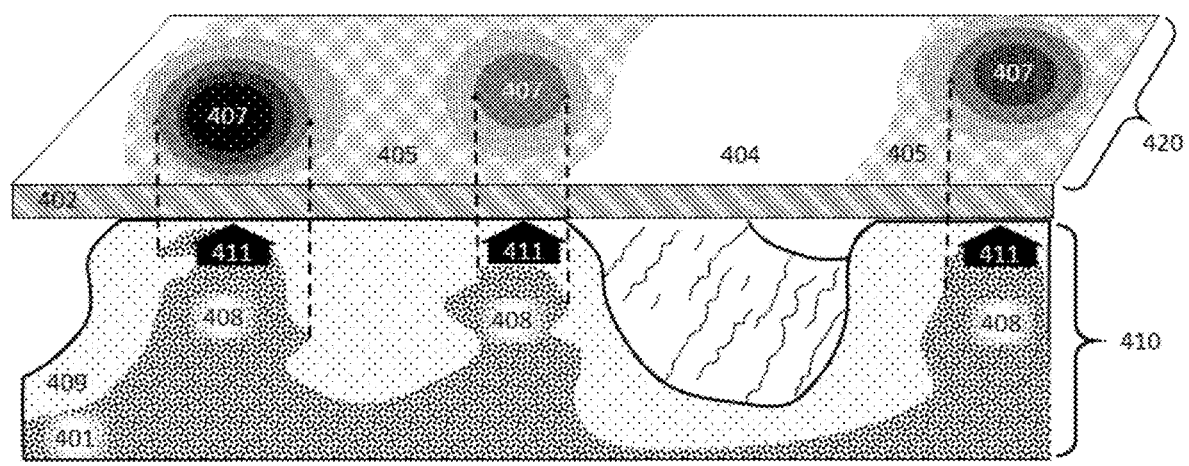
FIG. 4 illustrates a pressure distribution, in accordance with one or more implementations.

FIG. 4 illustrates a pressure distribution 400, in accordance with one or more implementations. Pressure distribution 400 may arise from the varying volumes and/or compositions of tissue that are compressed under regions of pressure sensitive membrane 402 that is arranged on an imaging surface. Pressure distribution 400 may be used as a basis for and/or may comprise the information representing the three-dimensional topography of the friction ridges of the subject. By way of non-limiting example, as the topographical ridge peaks 411 (e.g., corresponding to dermal papillae 408 and/or the highest elevation points of the friction ridges) of the friction ridges of the subject are compressed by pressure sensitive membrane 402 (e.g., as the subject presses his finger on the pressure sensitive membrane), topographical ridge peaks 411 may exert more force against pressure sensitive membrane 402 than surrounding tissue 409. A pressure distribution may map variations in friction ridge tissue height into different grayscale values and/or other values and/or colors illustrating corresponding changes in pressure. Topographical ridge peaks 411 may be illustrated in pressure distribution 400 as high pressure regions 407. Other, lower elevation portions of the friction ridges may be represented in pressure distribution 400 as lower pressure regions 405. The valley between the friction ridges may be represented on pressure distribution 400 as no pressure region 404. As such, pressure distribution 400 may represent a topographical map of the friction ridge surface of the subject.

In some implementations, one or more dermal papillae 408 in the tissue of the friction ridges may have a higher modulus of elasticity than the surrounding epidermal tissue 409. As the friction ridge tissue is compressed against pressure sensitive membrane 402, dermal papillae 408 may exert a higher local pressure (e.g., illustrated as high pressure regions 407) against pressure sensitive membrane 402. As such, pressure distribution 400 may comprise information representing the three-dimensional topography of the friction ridges of the subject that may represent and/or indicate the tissue composition and/or locations of one or more dermal papillae (in additional to and/or instead of indicating the height and/or elevation of the friction ridge tissue).

Figure 5:
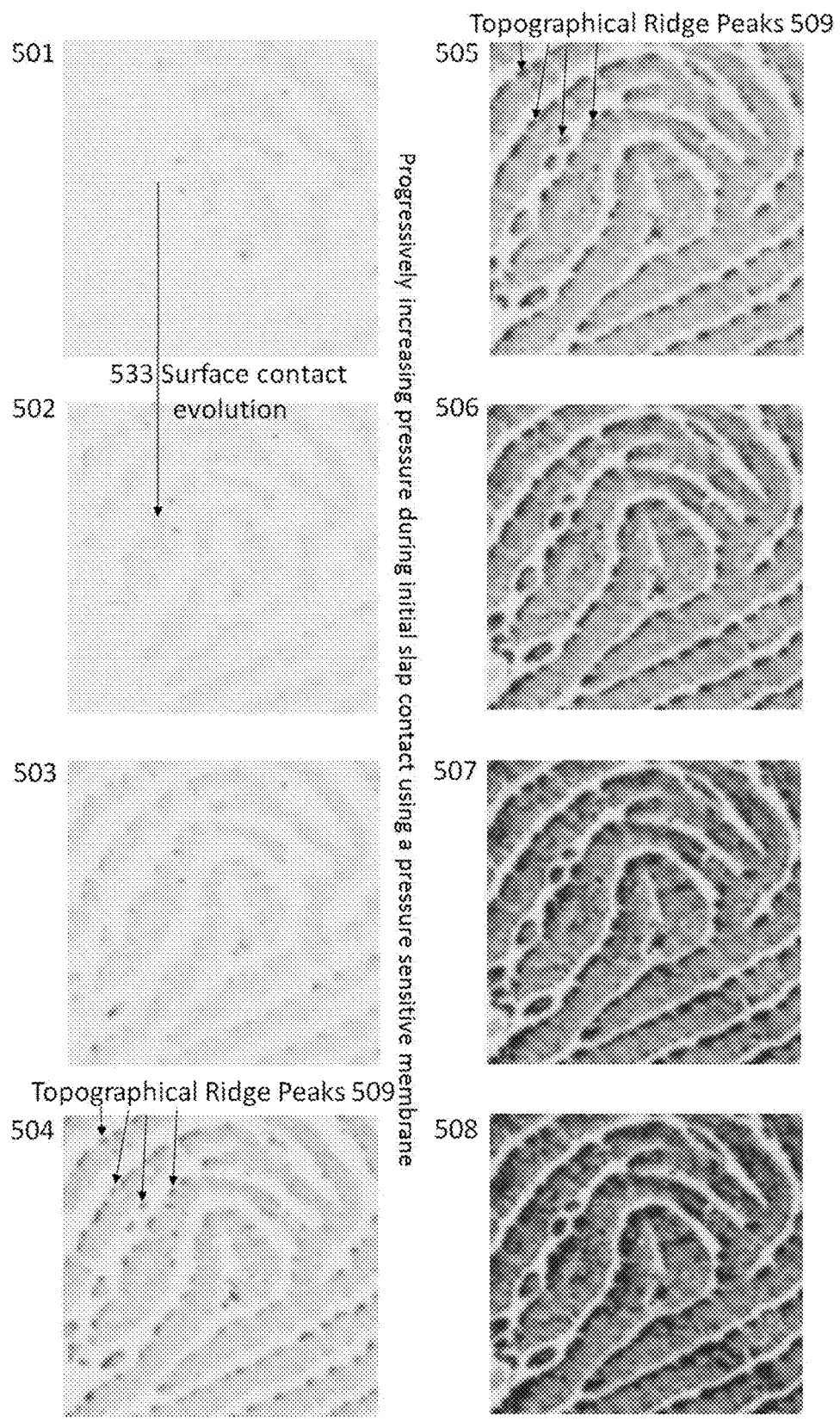
FIG. 5 illustrates a series of images captured by a TIR-based imaging system having a pressure sensitive membrane, in accordance with one or more implementations.

FIG. 5 illustrates a series of images captured by a TIR-based imaging system having a pressure sensitive membrane, in accordance with one or more implementations. Images 501-508 may include a series of images captured by a TIR-based imaging system having a pressure sensitive membrane. In some implementations, images 501-508 may include video images. Images 501-508 may illustrate progressively increasing pressure as a subject presses their finger (e.g., for a slap capture, etc.) on a pressure sensitive membrane arranged on an imaging surface of a TIR-based imaging system. Images 501-508 may be numbered and/or presented in sequential order based on their relative capture time. As such, image 501 may represent an image captured before images 502-508. Image 508 may be captured after images 501-507. One or more of images 501-508 may be the basis for and/or comprise the information representing the three-dimensional topography of the friction ridges of the subject from which one or more level III features may be identified. By way of non-limiting example, one or more topographical ridge peaks 509 may be identifiable in image 504, image 505, and/or other images, and/or a comparison of one or more of image 504, image 505, and/or other images.

Figure 6:
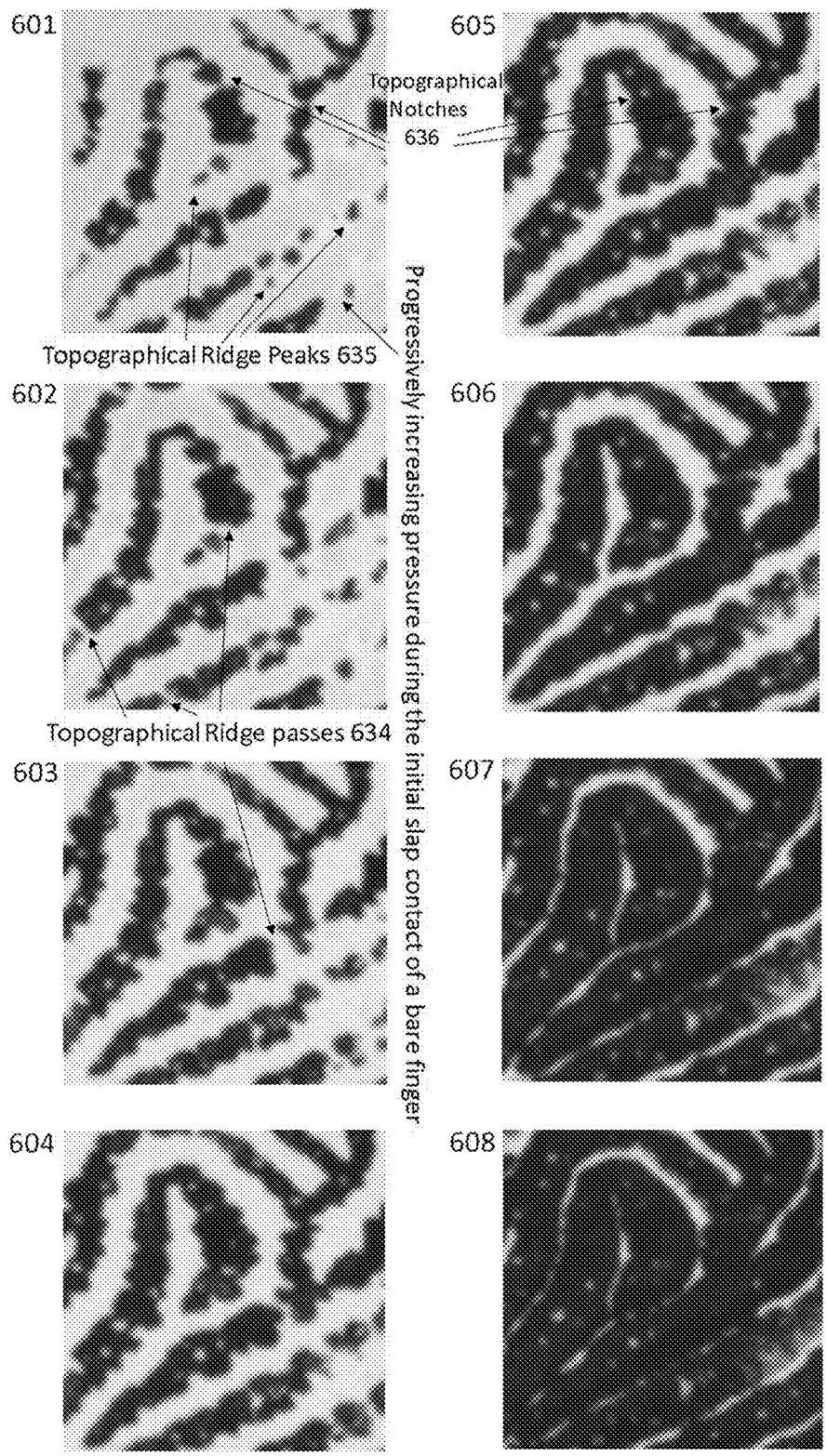
FIG. 6 illustrates a series of images captures by a TIR-based imaging system, in accordance with one or more implementations.

FIG. 6 illustrates a series of images captures by a TIR-based imaging system, in accordance with one or more implementations. Images 601-608 may include a series of images captured by a TIR-based imaging system without a pressure sensitive membrane. In some implementations, images 601-608 may include video images.

Images 601-608 may illustrate progressively increasing applied pressure as a subject presses their finger (e.g., for a slap capture, etc.) on an imaging surface of a TIR-based imaging system. Images 601-608 may be numbered in sequential order based on their relative capture time. As such, image 601 may represent an image captured before images 602-608. Image 608 may be captured after images 601-607. One or more of images 601-608 may be the basis for and/or comprise the information representing the three-dimensional topography of the friction ridges of the subject from which one or more level III features may be identified. By way of non-limiting example, one or more topographical ridge peaks 635 may be identifiable in image 601 and/or other images 602-608, and/or a comparison of image 601 and/or other images 602-608. One or more topographical ridge passes 634 may be identifiable in one or more of image 602, image 603, and/or other images 601-608, and/or a comparison of image 602, image 603, and/or other images 601-608. In some implementations, one or more topographical notches 636 may be identifiable in one or more of image 601, image 605, and/or other images 601-608, and/or a comparison of image 606, image 605, and/or other images 601-608.

Figure 7:
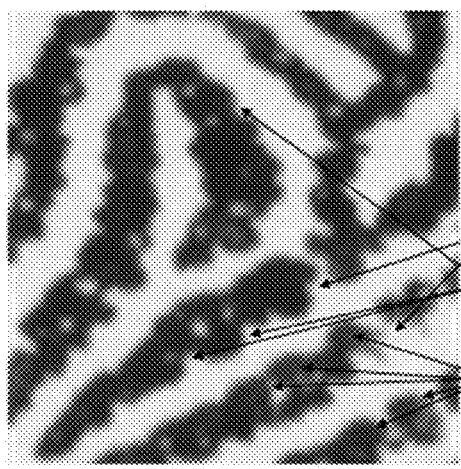
FIG. 7 illustrates a comparison of a friction ridge signature captured via one type of friction ridge signature technology, and information representing the three-dimensional topography of the friction ridges of the subject, in accordance with one or more implementations.
Figure 7:
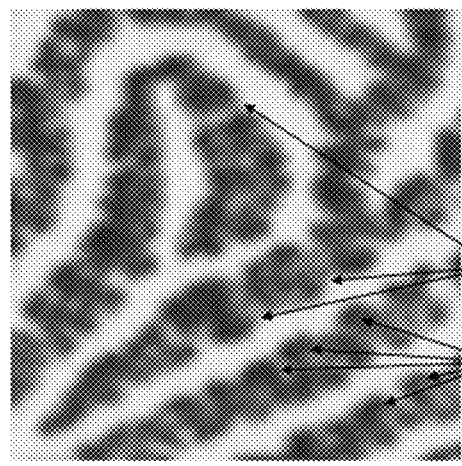
Figure 7:
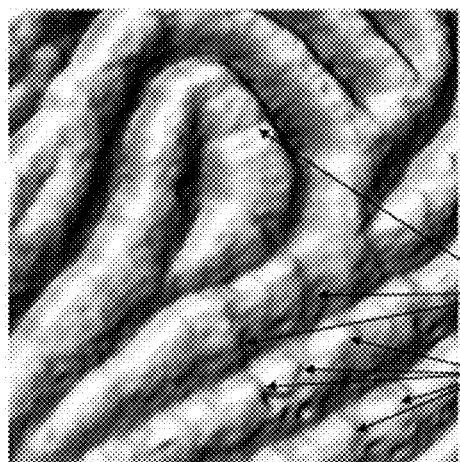

FIG. 7 illustrates a comparison of a friction ridge signature captured via one type of friction ridge signature technology, and information representing the three-dimensional topography of the friction ridges of the subject. Image 710 may illustrate a single frame friction ridge signature captured via a TIR-based imaging system using standard image processing. Image 720 may illustrate information representing the three-dimensional topography of the friction ridges of the subject. Image 720 may, for example, be an image captured by a total internal reflection based imaging system having a pressure sensitive membrane, and/or may be generated based on one or more images captured by a total internal reflection based imaging system having a pressure sensitive membrane. In image 710, one or more topographical ridge peaks, topographical ridge notches, and/or topographical ridge passes may not be visible and/or may be obscured because image 710 does not represent the topography of the friction ridges of the subject. For example, one or more merged topographical peaks 715 may be obscured and/or may merge together in image 710. By way of another example, one or more topographical ridge passes may by obscured and/or missing (e.g., missing topographical ridge passes 714 and/or false ridge breaks 713) in image 410. As such, the level III features (e.g., one or more topographical ridge peaks, topographical ridge notches, and/or topographical ridge passes) described herein may not be consistently identifiable in image 710 leading to unreliable and/or inconsistent results.

Image 720 on the other hand, may reliably depict one or more one or more topographical ridge peaks, topographical ridge notches, and/or topographical ridge passes enabling their use and level III identification features for fingerprints. In image 720, one or more topographical ridge peaks 707 and/or topographical ridge passes 724 may visible. As such, image 720 may represent the topography of the friction ridges of the subject.

In image 720, the higher pressure regions (e.g., which may be recorded as darker gray scale values which may be surrounded by lighter regions) may correlate with raised features of the friction ridge such as one or more topographical ridge peaks 707. Topographical ridge passes 724 may appear in image 720 as lighter gray paths across a darker friction ridge.

In some implementations, image 720 may be captured via a TIR-based imaging system having a pressure sensitive membrane. Image 720 may be one image of one or multiple images, or an aggregated representation of images, that comprise the information representing the three-dimensional topography of the friction ridges of the subject. As such, the level III features (e.g., one or more topographical ridge peaks, topographical ridge notches, and/or topographical ridge passes) described herein may be consistently identifiable in image 720 leading to reliable and/or consistent results.

Image 730 illustrates a three-dimensional rendering of friction ridges of a subject (e.g., the same friction ridges depicted in image 710, and image 720). Image 730 may be a three dimensional rendering of information representing the three-dimensional topography of the friction ridges of the subject and/or may be a pressure map of the friction ridges of the subject.

Returning to FIG. 1, feature identification component 114 may be configured to identify one or more level III features of the friction ridge signature of the subject. Feature identification component 114 may be configured to identify one or more level III features based on the information representing the three-dimensional topography of the friction ridges of the subject, and/or other information. The one or more level III features may include one or more topographical ridge peaks, topographical ridge notches, topographical ridge passes, pores, and/or other features. Feature identification component 114 may be configured to identify one or more level III features in a variety of ways. The examples of one or more methods by which feature identification component 114 may identify one or more topographical ridge peaks, topographical ridge notches, topographical ridge passes, pores, and/or other features based on information representing the three-dimensional topography of the friction ridges of the subject are intended to demonstrate various aspects of the disclosure by way of examples. The examples are intended to be illustrative and non-limiting, and other suitable methods are contemplated. In some implementations, the method by which feature identification component 114 identifies one or more topographical ridge peaks, topographical ridge notches, topographical ridge passes, pores, and/or other features may vary based on the type of the information representing the three-dimensional topography of the friction ridges of the subject.

By way of non-limiting example, one or more topographical ridge peaks may be identified by identifying regions of locally higher signal levels (e.g., acquired via a pressure sensitive membrane, and/or other sensors). The signal levels may be indicated in terms of optical grayscale values, electrical property values, or other sensor output levels. Areas with locally higher output signal levels and/or darker gray scales may be assigned higher relative pressure values. As such, areas with locally higher output signal levels and/or darker gray scales may correspond to one or more topographical ridge peaks (e.g., due to higher elevations and/or one or more dermal papillae). One or more topographical ridge passes may be identified by identifying regions of locally lower signal levels across one or more ridges. Areas with locally lower output signal levels and/or lighter gray scales that run across one or more ridges surrounded by higher output signals and/or darker gray scales on at least two sides (e.g., depicting a lower ridge which may generally run perpendicular to the direction of the friction ridge on which it is located) may correspond to one or more topographical ridge passes.

In some implementations, responsive to the information representing the three-dimensional topography of the friction ridges of the subject including a grayscale representation of a pressure distribution, an uphill gradient may refer to the direction in which the gray scale values are changing from light to dark and/or a downhill gradient may refer to a direction in which the gray scale values are changing from dark to light. An uphill gradient may correlate with directions of increasing local applied pressure (e.g., to the pressure sensitive membrane) and/or increasing local ridge height (e.g., corresponding to increasing surface area of the friction ridges in contact with an imaging surface over time as the subject presses their finger on an imaging surface). A downhill gradient may correlate with directions of decreasing local applied pressure (e.g., to the pressure sensitive membrane) and/or decreasing local ridge height (e.g., corresponding to less and/or decreasing surface area of the friction ridges in contact with an imaging surface).

Figure 8:
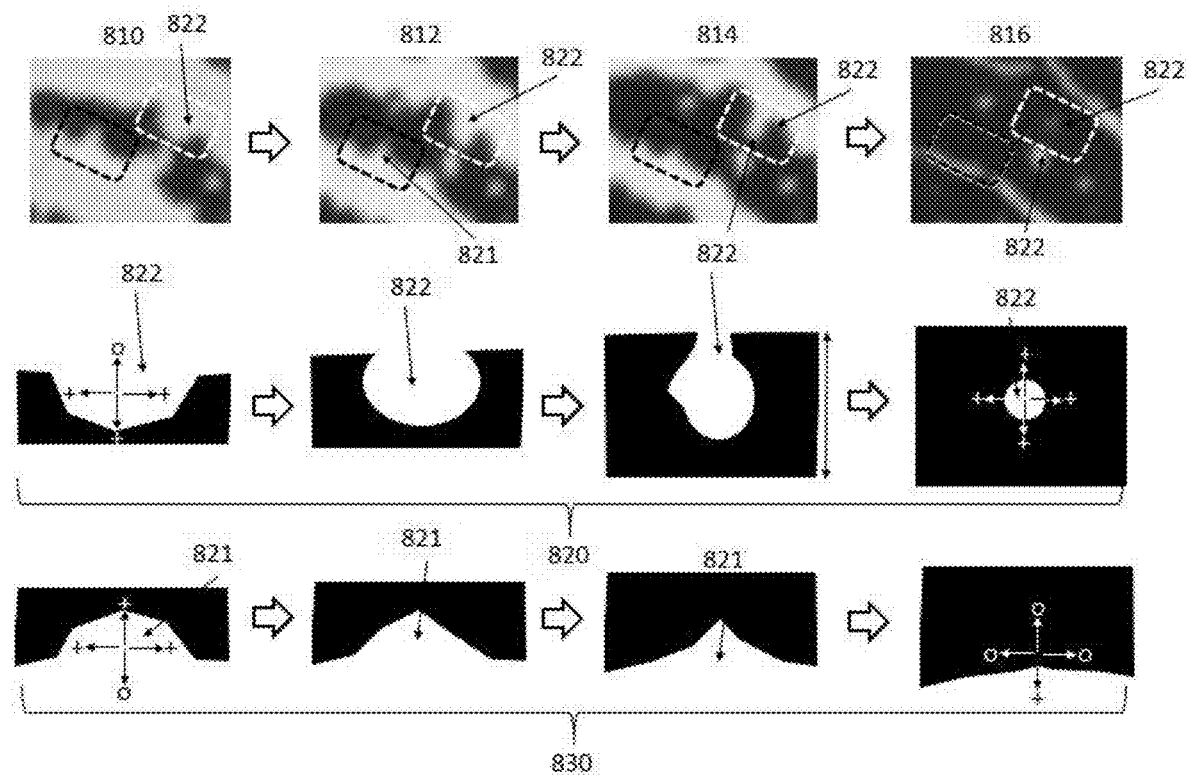
FIG. 8 illustrates identification of a pore and/or a topographical notch based on information representing the three-dimensional topography of the friction ridges of the subject, in accordance with one or more implementations.

FIG. 8 illustrates an example of how a pore and/or a topographical notch may be identified (e.g., by feature identification component that same as or similar to feature identification component 114) based on information representing the three-dimensional topography of the friction ridges of the subject. The information representing the three-dimensional topography of the friction ridge of the subject may include a sequence of images 810-816 captured over time via a TIR-based imaging system. Pore 822 may be identified responsive to identification of uphill gradients in 3 or 4 directions (e.g., the directions being separated by ninety degrees and/or approximately ninety degrees) in earlier images 810-814 and exhibits uphill gradients (+) in four directions (e.g., the four directions being separated by ninety degrees and/or approximately ninety degrees and/or comprising the positive and negative directions of two orthogonal axes that intersect at a pore location) in later image 816. The progression of pore 822 as time, the area of the imaging surface engaged by the friction ridges of the subject, and/or pressure applied by the subject increases may be illustrated by pore evolution 820. As illustrated, pore 822 may appear to be an open pore in images 810-814, but then may be correctly identified as a closed pore in image 816. Topographical notch 821 may be identified responsive to identification of an uphill gradient (+) in three directions (e.g., the directions being separated by ninety degrees and/or approximately ninety degrees) in earlier images 810-814 that changes to exhibit uphill gradients in one or two directions (e.g., the directions being separated by ninety degrees and/or approximately ninety degrees) in later image 816. The progression of topographical notch 821 as time, the area of the imaging surface engaged by the friction ridges of the subject, and/or pressure applied by the subject increases may be illustrated by notch evolution 830. Continuing the non-limiting use example illustrated in FIG. 8, topographical pass (not illustrated) may be identified as a feature which exhibits uphill gradients (+) in 2 opposite directions, and which is inside and roughly perpendicular to a friction ridge line. Conversely, a valley may also exhibit uphill gradients in 2 opposite directions, but a valley may be located outside of and/or roughly parallel to friction ridge lines. Continuing the non-limiting use example illustrated in FIG. 8, topographical ridge peak (not illustrated) may be identified as a feature which exhibits downhill gradients (+) in four directions (e.g., the four directions being separated by ninety degrees and/or approximately ninety degrees and/or comprising the positive and negative directions of two orthogonal axes that intersect at a topographical ridge peak).

Returning to FIG. 1, feature identification component 114 may be configured to identify one or more level III features of the friction ridge signature of the subject based on one or more of a topographical map, one or more cross sectional shapes of the friction ridge pattern at different elevations, a series of images captured over a time period, information generated based on the series on images captured over a time period, and/or other information. One or more topographical ridge peaks may be identified by feature identification component 114 based on an surface area of the friction ridges of the subject in contact with the imaging surface at different points in time during the process of initial contact between a finger and the imaging surface. By way of non-limiting example, the pressure applied by the finger may be monotonically increasing, and/or the distance between the imaging surface and the friction ridges of the subject (and/or the epidermal and/or dermal features of the finger) is monotonically decreasing. As such, regions of the friction ridge pattern of the subject that are higher, relative to low fingerprint valleys, may come in contact with the imaging surface first. Progressively lower regions of the ridge may sequentially contact the imaging surface during the time period in which the sequence of images are captured (e.g., and/or in which a video capture runs). In some implementations, imaging processing algorithms may include methods of comparing sequential images to identify areas of new contact between the finger and the imaging surface (e.g., changes in surface area of the imaging surface engaged by the friction ridges of the subject). By way of non-limiting example, the information representing the three-dimensional topography of the friction ridges may include a reconstruction of the topography of the friction ridges based on an assignment of a monotonically decreasing height value corresponding with all new pixels that became darker during the corresponding monotonically increasing timestamp values of that set of images. Other suitable methods may exist and are contemplated by the present application.

Matching component 116 may be configured to compare one or more of the topographical ridge peaks, the topographical ridge notches, the topographical ridge passes, the pores, and/or other features of the friction ridge signature of the subject with one or more topographical ridge peaks, topographical ridge notches, topographical ridge passes, pores, and/or other features of a second friction ridge signature. Matching component 116 may be configured to determine whether the friction ridge signature of the subject matches the second friction ridge signature. Matching component 116 may determine whether the friction ridge signature of the subject matches a second friction ridge signature based on the identification of one or more (e.g., by way of non-limiting example, at least 16 for a given portion of a friction ridge signature) topographical ridge peaks, topographical ridge notches, topographical ridge passes, pores, and/or other features by feature identification component 116.

Processor(s) 124, imaging system(s) 104, external resources 128, and/or other components may be operatively linked via one or more electronic communication links. For example, such electronic communication links may be established, at least in part, via a network 130 such as the Internet and/or other networks. It will be appreciated that this is not intended to be limiting, and that the scope of this disclosure includes implementations in which processor(s) 124, imaging system(s) 104, external resources 128, and/or other components may be operatively linked via some other communication media.

In some implementations, a given imaging system 104 may include the one or more processor(s). External resources 128 may include sources of information, hosts and/or providers outside of system 100, external entities participating with system 100, and/or other resources.

In some implementations, processor(s) 124 is configured to provide information processing capabilities. As such, processor(s) 124 may include one or more of a digital processor, an analog processor, a digital circuit designed to process information, an analog circuit designed to process information, a state machine, and/or other mechanisms for electronically processing information. Although processor(s) 124 is shown in FIG. 1 as a single entity, this is for illustrative purposes only. In some implementations, processor(s) 124 may include a plurality of processing units. These processing units may be physically located within the same device (e.g., within imaging system 104), or processor(s) 124 may represent processing functionality of a plurality of devices operating in coordination. Processor(s) 124 may be configured to execute components 112, 114, 116 and/or other components. Processor(s) 124 may be configured to execute components 112, 114, 116, and/or other components by software; hardware; firmware; some combination of software, hardware, and/or firmware; and/or other mechanisms for configuring processing capabilities on processor(s) 124.

It should be appreciated that although components 112, 114, 116 are illustrated in FIG. 1 as being co-located within a single processing unit, in implementations in which processor(s) 124 includes multiple processing units, one or more of components 112, 114, 116 may be located remotely from the other components. The description of the functionality provided by the different components 112, 114, 116 described below is for illustrative purposes, and is not intended to be limiting, as any of components 112, 114, 116 may provide more or less functionality than is described. For example, one or more of components 112, 114, 116 may be eliminated, and some or all of its functionality may be provided by other ones of components 112, 114, and/or 116. As another example, processor(s) 124 may be configured to execute one or more additional components that may perform some or all of the functionality attributed below to one of components 112, 114, 116.

Figure 9:
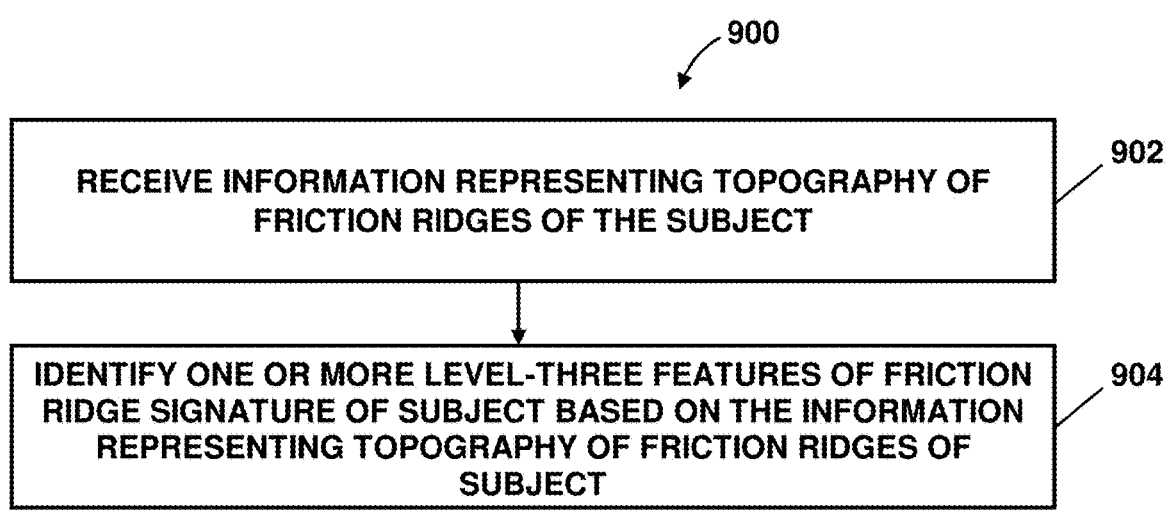
FIG. 9 illustrates a method for identifying features of a friction ridge signature of a subject based on information representing a topography of friction ridges of the subject, in accordance with one or more implementations.

FIG. 9 illustrates a method 900 for identifying features of a friction ridge signature of a subject based on information representing a topography of friction ridges of the subject, in accordance with one or more implementations. The operations of method 900 presented below are intended to be illustrative. In some implementations, method 900 may be accomplished with one or more additional operations not described, and/or without one or more of the operations discussed. Additionally, the order in which the operations of method 900 are illustrated in FIG. 9 and described below is not intended to be limiting.

In some implementations, method 900 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 900 in response to instructions stored electronically on an electronic storage medium. The one or more processing devices may include one or more devices configured through hardware, firmware, and/or software to be specifically designed for execution of one or more of the operations of method 900.

At operation 902, information representing the three-dimensional topography of the friction ridges of the subject may be received. The information representing the three-dimensional topography may include three dimensional information for the friction ridges of the subject. Operation 902 may be performed by an information component the same as or similar to information component 112 (illustrated in FIG. 1).

At operation 904, one or more level III features of the friction ridge signature of the subject may be identified. One or more of the level III features may be identified based on the information representing the three-dimensional topography of the friction ridges of the subject. The one or more level III features may include one or more topographical ridge peaks, topographical ridge notches, topographical ridge passes, pores, and/or other features. Operation 904 may be performed by a feature identification component the same as or similar to feature identification component 114 (illustrated in FIG. 1).

Figure 10:
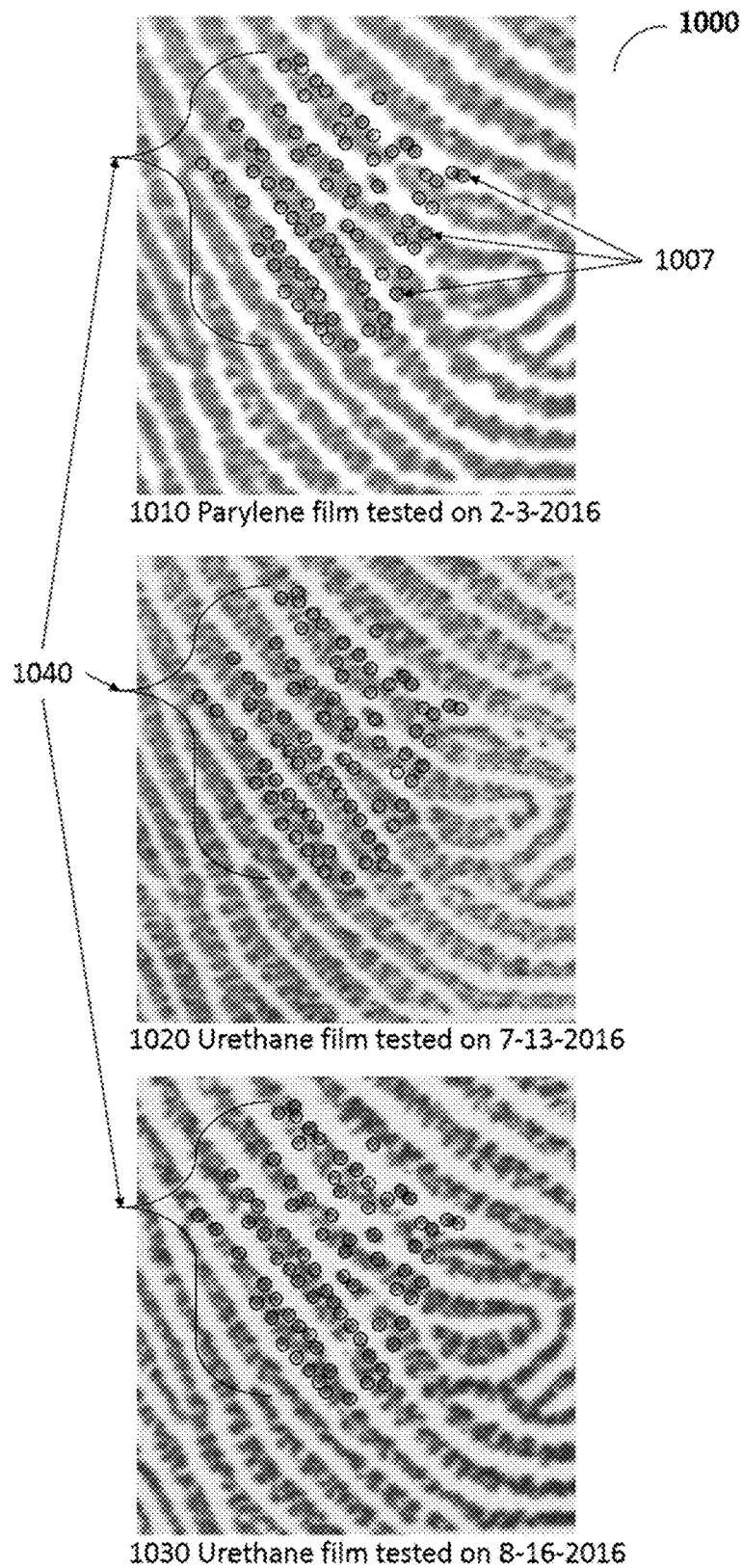
FIG. 10 illustrates a persistent pattern of level three topographical ridge peaks in a portion of the friction ridge signature of a subject using a pressure sensitive membrane with a TIR-based imaging system, in accordance with one or more implementations.

FIG. 10 illustrates experimental data that recorded a fixed pattern of level III topographical ridge peaks. Fixed pattern 1040 of 81 level III topographical ridge peaks 1007 was found to be persistent in a subject's friction ridge signature over a six month period 1000. The pressure maps of FIG. 10 were acquired using three different pressure sensitive membranes with a TIR-based live scan device. The pressure map 1010 used a pressure sensitive membrane made out of parylene and tested on Feb. 3, 2016. The pressure map 1020 used a pressure sensitive membrane made out of urethane and tested on Jul. 13, 2016. The pressure map 1030 used a pressure sensitive membrane made out of urethane and tested on Aug. 16, 2016. Whereas a typical entire fingerprint about 20 mm wide may yield 30-40 level-two features, the 81 level-three features depicted were all contained in a region less than 3 mm across. The fixed pattern confirms that these level-three features can be used to match friction ridge signatures accurately.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to identify features of a friction ridge signature of a subject based on information representing a three-dimensional topography of friction ridges of the subject, the system comprising:
    a processor configured to receive information representing the three-dimensional topography of the friction ridges of the subject, wherein the information representing the three-dimensional topography of the friction ridges of the subject includes a three-dimensional point cloud;
    wherein the processor is configured by machine-readable instructions to identify one or more level-three features of the friction ridge signature of the subject based on the information representing the three-dimensional topography of the friction ridges of the subject;
    wherein at least one of the level-three features is a three-dimensional structure comprising one or more topographical ridge passes; and
    wherein each of the one or more topographical ridge passes is a path across one of the friction ridges that includes one or more of: a region in the three-dimensional point cloud having an elevation level that is higher than valleys nearest the one of the friction ridges and lower than peaks nearest the one of the friction ridges or a region in the three-dimensional point cloud having a series of points that are higher than the valleys nearest the one of the friction ridges and lower than the peaks nearest the one of the friction ridges.

2. The system of claim 1, wherein the level-three features include one or more topographical ridge peaks, and/or topographical ridge notches.

3. The system of claim 2, wherein one or more of the topographical ridge peaks are identified based on a region in the three-dimensional point cloud having a higher point and/or elevation level than surrounding regions.

4. The system of claim 2, wherein:
    the level-three features include one or more topographical ridge notches; and
    one or more of the topographical ridge notches are identified based on a region in the three-dimensional point cloud of multiple points having a local positive curvature in the direction towards the nearest valley.

5. The system of claim 1, wherein the level-three features include one or more pores.

6. The system of claim 5, wherein one or more pores are identified based on one or more of the following criteria: a region in the three-dimensional point cloud having an elevation level that is lower than the surrounding friction ridge elevation in all directions and/or a region in the three-dimensional point cloud having points that are lower than the surrounding friction ridge in all directions.

7. The system of claim 1, wherein the information representing the three-dimensional topography of the friction ridges is generated based on a series of images captured over a time period by an imaging system having an imaging surface.

8. The system of claim 1, wherein the three-dimensional point cloud is generated based on a series of images captured over a time period.

9. The system of claim 1, wherein the three-dimensional point cloud is generated based on one or more images captured by an imaging system having a pressure sensitive membrane.

10. A method for identifying features of a friction ridge signature of a subject based on information representing a topography of friction ridges of the subject, the friction ridges of the subject varying in elevation and forming a friction ridge pattern having three dimensional features reflected in the friction ridge signature of the subject, the method being implemented by one or more processors, the method comprising:
   receiving information representing the three-dimensional topography of the friction ridges of the subject, wherein the information representing the three-dimensional topography of the friction ridges of the subject includes a three-dimensional point cloud;
   identifying one or more level-three features of the friction ridge signature of the subject based on the information representing the three-dimensional topography of the friction ridges of the subject;
   wherein at least one of the level-three features is a three-dimensional structure comprising one or more topographical ridge passes; and
   wherein each of the one or more topographical ridge passes is a path across one of the friction ridges that includes one or more of: a region in the three-dimensional point cloud having an elevation level that is higher than valleys nearest the one of the friction ridges and lower than peaks nearest the one of the friction ridges or a region in the three-dimensional point cloud having a series of points that are higher than the valleys nearest the one of the friction ridges and lower than the peaks nearest the one of the friction ridges.

11. The method of claim 10, wherein the level-three features include one or more topographical ridge peaks, and/or topographical ridge notches.

12. The method of claim 11, wherein one or more of the topographical ridge peaks are identified based on a region in the three-dimensional point cloud having a higher point and/or elevation level than surrounding regions.

13. The method of claim 11, wherein:
   the level-three features include one or more topographical ridge notches; and
   one or more of the topographical ridge notches are identified based on a region in the three-dimensional point cloud of multiple points having a local positive curvature in the direction towards the nearest valley.

14. The method of claim 10, wherein the level-three features include one or more pores.

15. The method of claim 14, wherein one or more pores are identified based on one or more of the following criteria: a region in the three-dimensional point cloud having an elevation level that is lower than the surrounding friction ridge elevation in all directions and/or a region in the three-dimensional point cloud having points that are lower than the surrounding friction ridge in all directions.

16. The method of claim 10, wherein the information representing the three-dimensional topography of the friction ridges is generated based on a series of images captured over a time period by an imaging system having an imaging surface.

17. The method of claim 10, wherein the three-dimensional point cloud is generated based on a series of images captured over a time period.

18. The method of claim 10, wherein the three-dimensional point cloud is generated based on one or more images captured by a total internal reflection based imaging system having a pressure sensitive membrane.

* * * * *